(12) United States Patent
Yuan et al.

(10) Patent No.: US 6,281,359 B1
(45) Date of Patent: *Aug. 28, 2001

(54) AMINOMETHYL PHENYL PYRIDINE DERIVATIVES

(75) Inventors: Jun Yuan, Clinton; Andrew Thurkauf, Danbury, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/457,409

(22) Filed: Jun. 1, 1995

Related U.S. Application Data

(63) Continuation of application No. 08/344,497, filed on Nov. 23, 1994.

(51) Int. Cl.$^7$ .................................................. C07D 401/06
(52) U.S. Cl. .................... 544/360; 540/575; 546/148; 546/256; 546/286; 546/304
(58) Field of Search .................... 546/148, 256, 546/286, 304; 544/360; 540/575

(56) References Cited

U.S. PATENT DOCUMENTS

| | | | |
|---|---|---|---|
| 4,698,340 | 10/1987 | Kawanishi et al. | 514/222 |
| 4,727,073 | 2/1988 | Kawanishi et al. | 514/252 |
| 4,906,642 | 3/1990 | Kampe et al. | 514/318 |
| 5,912,350 * | 6/1999 | Yuan et al. | 546/194 |

FOREIGN PATENT DOCUMENTS

| | | |
|---|---|---|
| 0177287 | 4/1986 | (EP) . |
| 0237908 | 9/1987 | (EP) . |
| 0237962 | 9/1987 | (EP) . |

OTHER PUBLICATIONS

Garg, S., (1978), "Antifertility Effects of Substituted Biphenyl Derivatives," *Chemical Abstracts*, vol. 89, No. 13, p. 121, Abstract No. 100486.

Garg, S., (1978), "Antifertility Effect of Substituted Biphenyl Derivatives in Female Rats," *Indian J. Med. Res.*, vol. 67, No. 3, pp. 392–396.

Zhang, Y. et al., (1987), "Nonsteroidal Antiinflammatory Drugs," *Chemical Abstracts*, vol. 106, No. 25, p. 597, Abstract No. 119384a.

Zhang, Y. et al. (1986), Studies on Nonsteroidal Antiinflammatory Drug: Synthesis and Biological Activity of 4–Hydroxy–3–Aminomethyl–Diphenyl and 4(2)–Cyclohexyl–2(4)–Aminomethyl–Phenol Derivatives, *Acta Pharmaceutica Sinica*, vol. 21, No. 5, pp. 345–355.

Smirnov, L., (1971), "Chem. of 2–Aryl–Subst. 3–Hydroxypyridines.," *Chemical Abstracts*, vol. 74, No. 15, p. 430, Abstract No. 76279w.

Smirnov, L., (1970), "Chem. of 2–Aryl–Subst. 3–Hydroxypyridines.," *Izv. Akad. Nauk. SSSR, Ser. Khim.*, No. 8, pp. 1845–1851.

CA 108:5864, 1987.*

\* cited by examiner

*Primary Examiner*—Richard L. Raymond
*Assistant Examiner*—Deepak Rao
(74) *Attorney, Agent, or Firm*—McDonnell Boehnen Hulbert & Berghoff; Steven J. Sarussi

(57) ABSTRACT

Disclosed are compounds of the formula:

where
S and V are various organic or inorganic substituents;
G and K are the same or different and represent N or CR' where R' is an organic or inorganic substituent;
R is hydrogen or an alkyl group;
$R_1$, X, Y, Z and T are organic or inorganic substituents; and
$R_2$ and $R_3$ represent hydrogen or organic substituents; or
$NR_2R_3$ together represents a heterocyclic ring system;

and the pharmaceutically acceptable salts thereof; which are highly selective partial agonists or antagonists at brain dopamine receptor subtypes and, thus, are useful in the diagnosis and treatment of affective disorders such as schizophrenia and depression as well as certain movement disorders such as Parkinsonism.

3 Claims, 2 Drawing Sheets

Compound 1

Compound 2

Compound 3

Compound 4

Compound 5

Compound 6

Compound 7

Compound 8

Compound 9

Compound 10

Compound 11

Compound 12

AMINOMETHYL PHENYL PYRIDINE DERIVATIVES

This is a continuation application of U.S. Ser. No. 08/344,497, filed Nov. 23, 1994.

BACKGROUND OF THE INVENTION

1. Field of the Invention

This invention relates to certain aminomethyl biphenyl, phenylpyridines and phenylpyrimidine derivatives which selectively bind to brain dopamine receptor subtypes. This invention also relates to pharmaceutical compositions comprising such compounds. It further relates to the use of such compounds in treating affective disorders such as schizophrenia and depression as well as certain movement disorders such as Parkinsonism.

2. Description of the Related Art

Schizophrenia or psychosis is a term used to describe a group of illnesses of unknown origin which affect approximately 2.5 million people in the United States. These disorders of the brain are characterized by a variety of symptoms which are classified as positive symptoms (disordered thought, hallucinations and delusions) and negative symptoms (social withdrawal and unresponsiveness). These disorders have an age of onset in adolescence or early adulthood and persist for many years. The disorders tend to become more severe during the patient's lifetime and can result in prolonged institutionalization. In the United States today, approximately 40% of all hospitalized psychiatric patients suffer from schizophrenia.

During the 1950's physicians demonstrated that they could successfully treat psychotic patients with medications called neuroleptics; this classification of antipsychotic medication was based largely on the activating (neuroleptic) properties of the nervous system by these drugs. Subsequently, neuroleptic agents were shown to increase the concentrations of dopamine metabolites in the brain suggesting altered neuronal firing of the dopamine system. Additional evidence indicated that dopamine could increase the activity of adenylate cyclase in the corpus striatum, an effect reversed by neuroleptic agents. Thus, cumulative evidence from these and later experiments strongly suggested that the neurotransmitter dopamine was involved in schizophrenia.

One of the major actions of antipsychotic medication is the blockade of dopamine receptors in brain. Several dopamine systems appear to exist in the brain and at least five classes of dopamine receptors appear to mediate the actions of this transmitter. These dopamine receptors differ in their pharmacological specificity and were originally classified upon these differences in the pharmacology of different chemical series. The butyrophenones, a class of compounds containing many potent antipsychotic drugs, were quite weak at the dopamine receptor that activated adenylate cyclase (now known as a D1 dopamine receptor). In contrast, they labelled other dopamine receptors (called D2 receptors) in the subnanomolar range and a third type, D3, in the nanomolar range. Two additional receptor subtypes have also been identified. D5, which is somewhat similar to the D1 receptor subtype, and D4 which is closely related to D3 and D2 receptor types. The phenothiazines, which include chlorpromazine, possess nanomolar affinity for all three types of dopamine receptors. Other drugs have been developed with great specificity for the D1 receptor subtype and for the D2 receptor subtype.

A group of drugs (such as sulpiride and clozapine) have been developed which display a lesser incidence of extrapyramidal side effects than classical neuroleptics. In addition, there is some indication that these drugs may be more beneficial in treating negative symptoms in some patients. Since all D2 blockers do not possess a similar profile, certain hypotheses underlying the differences have been investigated. One of the major differences among these various classes of antipsychotics has been in the anticholinergic actions of these drugs. The possibility also exists that the various doparmine receptor subtypes may be differentially distributed between the limbic areas, thought to mediate antipsychotic responses, and the motor areas of the brain. The existence of the D3, D4 and D5 and other as yet undiscovered dopamine receptors may contribute to this profile. Atypical antipsychotics have loosely been defined as those compounds which impart antipsychotic action without the concurrent motor impairment. Some of the atypical compounds possess similar activity at both D2, D3 and D4 receptors. The examples of this patent fall into this general class of molecules.

Using molecular biological techniques it has been possible to clone cDNAs coding for each of the pharmacologically defined dopamine receptors. There are at least two forms of D1-type receptors, which have been referred to as D1 and D5, and two forms of D2-type receptors, referred to now as D2 and D4 dopamine receptors. In addition, there is at least one form of D3 dopamine receptor. Examples from the aminomethyl biphenyl, aminomethyl phenylpyridines and aminomethyl phenylpyrimidines series of this patent possess differential affinities for each receptor subtype.

SUMMARY OF THE INVENTION

This invention provides novel compounds of Formula I which interact with dopamine receptor subtypes.

The invention provides pharmaceutical compositions comprising compounds of Formula I. The invention also provides compounds useful in treating affective disorders such as schizophrenia and depression as well as certain movement disorders such as Parkinsonism. Furthermore compounds of this invention may be useful in treating the extrapyramidyl side effects associated with the use of conventional neuroleptic agents. Since dopamine D3 and D4 receptor subtypes are concentrated in the limbic system (Taubes, *Science* (1994) 265, 1034) which controls cognition and emotion, compounds which interact with these receptors may have utility in the treatment of cognitive disorders. Such disorders may be the cognitive deficits which are a significant component of the negative symptoms (social withdrawal, and unresponsiveness) of schizophrenia. Other disorders involving memory impairment or attention deficit disorders may also be treated with the compounds of this invention that interact specifically with dopamine D3 and/or D4 receptor subtypes. Accordingly, a broad embodiment of the invention is directed to a compound of Formula I:

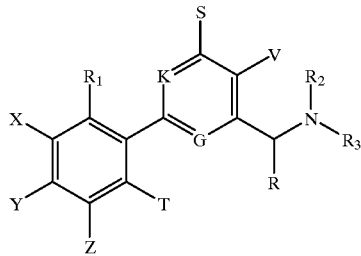

where
S and V are the same or different and represent hydrogen, halogen, hydroxy, phenyl, straight or branched chain lower alkyl having 1–6 carbon atoms, or straight or branched chain lower alkoxy having 1–6 carbon atoms;
G and K are the same or different and represent N or CR' where R' is hydrogen, halogen, straight or branched chain lower alkyl having 1–6 carbon atoms or straight or branched lower alkoxy having 1–6 carbon atoms;
R is hydrogen or straight or branched chain lower alkyl having 1–6 carbon atoms;
$R_1$, X, Y, Z and T are the same or different and represent hydrogen, halogen, cyano, hydroxy, straight or branched chain lower alkyl having 1–6 carbon atoms, straight or branched chain lower alkoxy having 1–6 carbon atoms or $SO_2R_4$ where $R_4$ is straight or branched chain lower alkyl having 1–6 carbon atoms or where $R_4$ is $NH_2$ or $NHCH_3$;
$R_2$ and $R_3$ are the same or different and represent hydrogen, straight or branched chain lower alkyl having 1–6 carbon atoms, aryl arylalkyl; or
$NR_2R_3$ together represent 2-(1,2,3,4-tetrahydroisoquinolinyl), either unsubstituted or mono or disubstituted with halogen, hydroxy, straight or branched chain lower alkyl having 1–6 carbon atoms, or straight or branched chain lower alkoxy having 1–6 carbon atoms; or
$NR_2R_3$ represents:

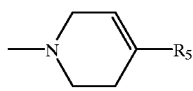

where $R_5$ is phenyl, either unsubstituted or mono or disubstituted by either halogen, hydroxy, straight or branched chain lower alkyl having 1–6 carbon atoms, or straight or branched chain lower alkoxy having 1–6 carbon atoms; or
$NR_2R_3$ represents

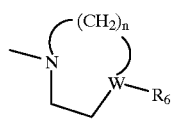

where W is N or CH; and
$R_6$ is phenyl, benzyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; and n is 1, 2 or 3.

The interaction of the aminomethyl biphenyl, aminomethyl phenylpyridines and aminomethyl phenylpyrimidine derivatives of the invention with dopamine receptor subtypes results in the pharmacological activities of these compounds. These compounds are highly selective partial agonists or antagonists at brain dopamine receptor subtypes or prodrugs thereof and are useful in the diagnosis and treatment of affective disorders such as schizophrenia and depression as well as certain movement disorders such as Parkinsonism. Furthermore, compounds of this invention are useful in treating the extrapyramidyl side effects associated with the use of conventional neuroleptic agents.

Thus, the invention encompasses methods for the treatment of neuropsychological disorders comprising administering to a patient having a neuropsychological disorder an amount of a compound according to Formula I effective to treat the neuropsychological disorder.

DETAILED DESCRIPTION OF THE INVENTION

Figure 1A:
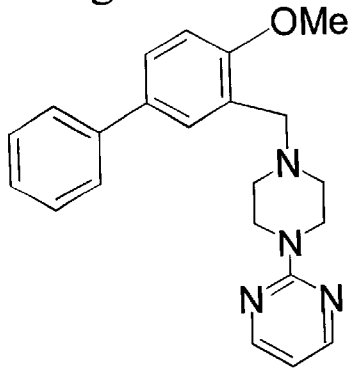
FIGS. 1A–1L show representative aminomethyl biphenyls, aminomethyl phenylpyridines and aminomethyl phenylpyrimidines of the present invention.

In addition to compounds of general formula I described above, the present invention further encompasses compounds of Formula II:

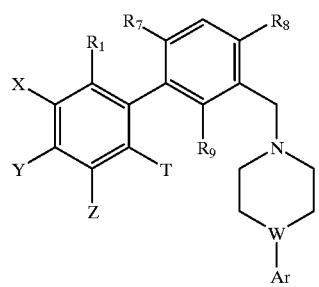

where $R_1$, X, Y, Z and T represent hydrogen or alkyl; $R_7$ and $R_8$ independently represent hydrogen or alkoxy; $R_9$ is hydrogen or alkyl; and W represents nitrogen or CH.

Preferred compounds of Formula I include those where W is N or CH; and $R_7$ is phenyl, pyridyl or pyrimidinyl, each of which is optionally mono or disubstituted with halogen, hydroxy, straight or branched chain lower alkyl having 1–6 carbon atoms, or straight or branched chain lower alkoxy having 1–6 carbon atoms.

Preferred compounds according to Formula II are those where $R_1$, X, Y, Z and T are hydrogen; $R_7$ and $R_8$ are different and represent hydrogen or alkoxy; W is CH; and Ar represents benzyl or phenyl. Other preferred compounds of Formula II are those where $R_1$, X, Y, Z and T are hydrogen; $R_7$ and $R_8$ are different and represent hydrogen or alkoxy; W is nitrogen; and Ar represents 2-pyridyl or pyrimidinyl.

The invention further encompasses compounds of Formula III:

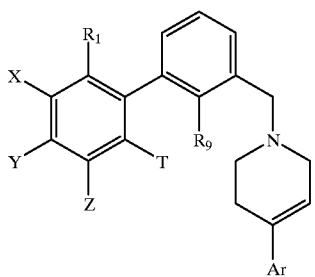

where $R_1$, X, Y, Z and T represent hydrogen or alkyl and $R_9$ represents hydrogen or alkyl.

Preferred compounds according to Formula III are those where $R_1$, X, Y, Z and T are hydrogen; $R_9$ represents hydrogen; and Ar represents benzyl or phenyl. Other preferred compounds of Formula III are those where $R_1$, X, Y, Z and T are hydrogen; $R_9$ represents hydrogen; and Ar represents 2-pyridyl or pyrimidinyl.

The invention further encompasses compounds of Formula IV:

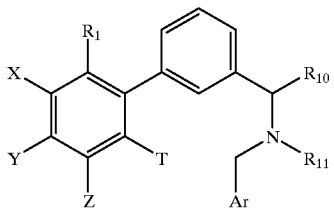

where $R_1$, X, Y, Z and T represent hydrogen or alkyl; and $R_{10}$ and $R_{11}$ independently represent hydrogen or alkyl.

Preferred compounds according to Formula IV are those where $R_1$, X, Y, Z and T are hydrogen; Ar represents phenyl; and $R_{10}$ and $R_{11}$ independently represent alkyl. Other preferred compounds of Formula IV are those where $R_1$, X, Y, Z and T are hydrogen; $R_{10}$ and $R_{11}$ independently represent methyl; and Ar represents phenyl.

The invention further encompasses compounds of Formula V:

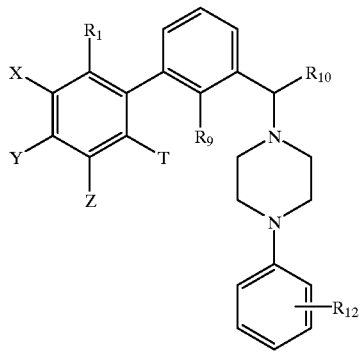

where $R_1$, X, Y, Z and T represent hydrogen or alkyl; $R_9$ is hydrogen or alkyl; $R_{10}$ represents hydrogen or alkyl; and $R_{12}$ represents alkoxy.

Preferred compounds according to Formula V are those where $R_1$, X, Y, Z and T are hydrogen; $R_9$ is hydrogen; $R_{10}$ represents alkyl and $R_{12}$ is an alkoxy group in the 2-position of the phenyl ring.

The invention further encompasses compounds of Formula VI:

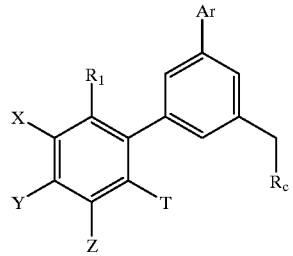

where $R_1$, X, Y, Z and T represent hydrogen or alkyl; and $R_c$ is a group of the formula:

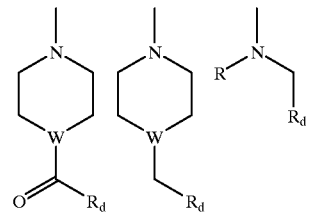

where

W is N or CH;

R represents alkyl; and $R_d$ represents pyridyl, pyrimidinyl, phenylalkyl, or phenyl optionally substituted with halogen, alkyl or alkoxy.

Preferred compounds according to Formula VI are those where $R_1$, X, Y, Z and T are hydrogen; Ar is optionally substituted phenyl and $R_c$ is a 4-substituted piperazin-1-yl or piperidin-1-yl group. Particularly preferred compounds of Formula VI are those where the 4-substituted piperazin-1-yl or piperidin-1-yl groups are substituted with optionally substituted phenyl, phenylalkyl, 2-pyridyl or 2-pyrimidinyl groups.

The invention further provides compounds of Formula VII:

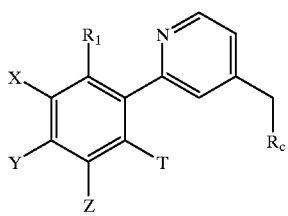

where $R_1$, X, Y, Z and T represent hydrogen or alkyl; and $R_c$ is a group of the formula:

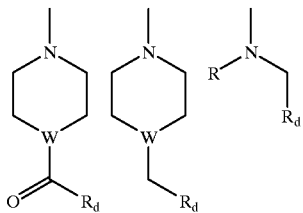

where
W is N or CH;
R represents alkyl; and
$R_d$ represents pyridyl, pyrimidinyl, phenylalkyl, or phenyl optionally substituted with halogen, alkyl or alkoxy.

Preferred compounds according to Formula VII are those where $R_1$, X, Y, Z and T are hydrogen; and $R_c$ is a 4-substituted piperazin-1-yl or piperidin-1-yl group. Particularly preferred compounds of Formula VII are those where the 4-substituted piperazin-1-yl or piperidin-1-yl groups are substituted with optionally substituted phenyl, phenylalkyl, 2-pyridyl or 2-pyrimidinyl groups.

The invention further provides compounds of Formula VIII:

VIII

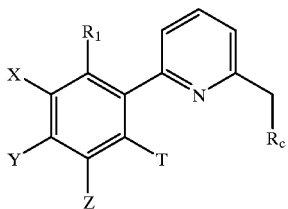

where $R_1$, X, Y, Z and T represent hydrogen or alkyl; and $R_c$ is a group of the formula:

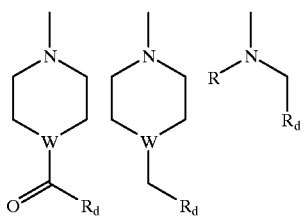

where
W is N or CH;
R represents alkyl; and
$R_d$ represents pyridyl, pyrimidinyl, phenylalkyl, or phenyl optionally substituted with halogen, alkyl or alkoxy.

Preferred compounds according to Formula VIII are those where $R_1$, X, Y, Z and T are hydrogen; and $R_c$ is a 4-substituted piperazin-1-yl or piperidin-1-yl group. Particularly preferred compounds of Formula VIII are those where the 4-substituted piperazin-1-yl or piperidin-1-yl groups are substituted with optionally substituted phenyl, phenylalkyl, 2-pyridyl or 2-pyrimidinyl groups.

The invention further provides compounds of Formula IX:

IX

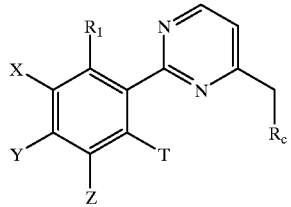

where $R_1$, X, Y, Z and T represent hydrogen or alkyl; and $R_c$ is a group of the formula:

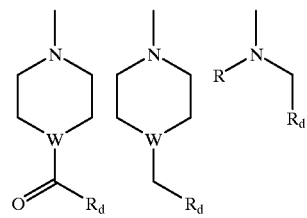

where
W is N or CH;
R represents alkyl; and
$R_d$ represents pyridyl, pyrimidinyl, phenylalkyl, or phenyl optionally substituted with halogen, alkyl or alkoxy.

Preferred compounds according to Formula IX are those where $R_1$, X, Y, Z and T are hydrogen; and $R_c$ is a 4-substituted piperazin-1-yl or piperidin-1-yl group. Particularly preferred compounds of Formula IX are those where the 4-substituted piperazin-1-yl or piperidin-1-yl groups are substituted with optionally substituted phenyl, phenylalkyl, 2-pyridyl or 2-pyrimidinyl groups. Still other preferred compounds of Formula IX are those where $R_c$ is N-benzyl-N-methylamino.

Figure 1B:
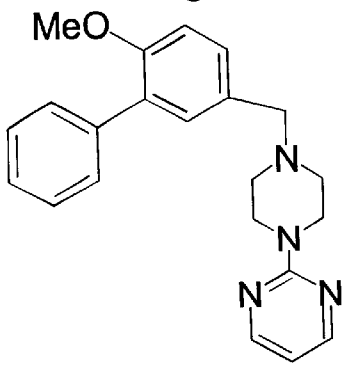
Figure 1C:
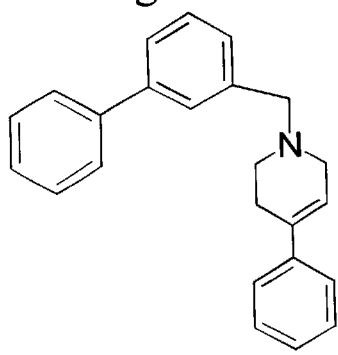
Figure 1D:
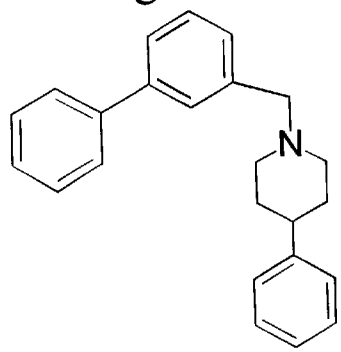
Figure 1E:
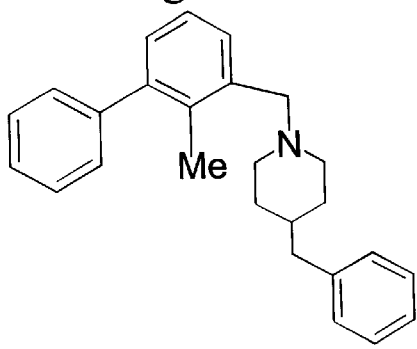
Figure 1F:
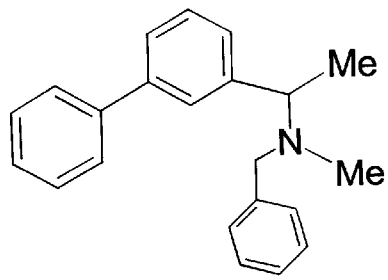
Figure 1G:
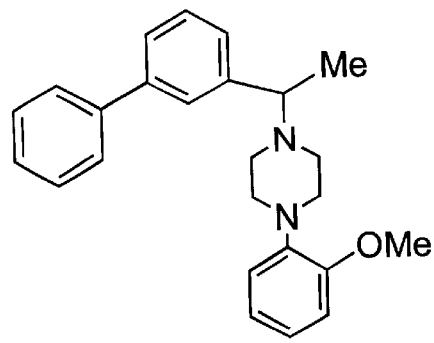
Figure 1H:
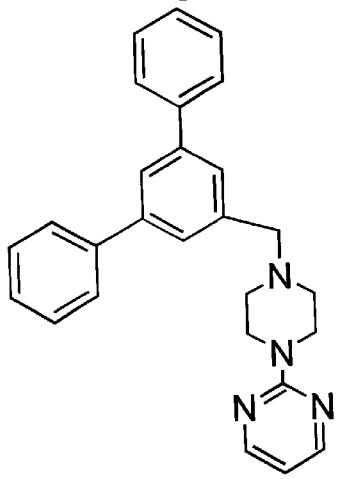
Figure 1I:
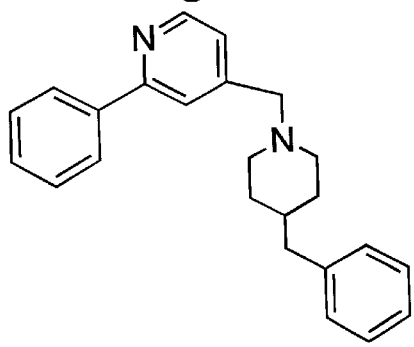
Figure 1J:
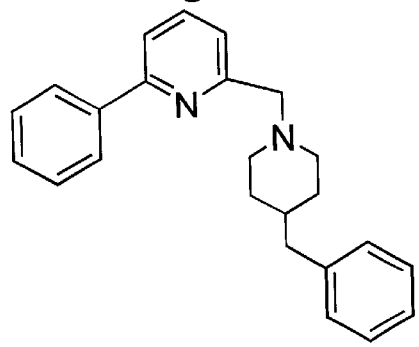
Figure 1K:
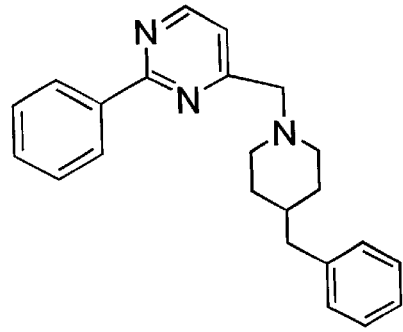
Figure 1L:
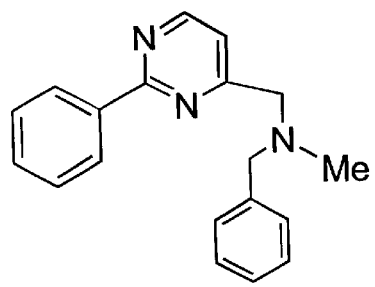

Representative compounds of the present invention, which are encompassed by Formula I, include, but are not limited to the compounds in FIG. 1 and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By aryl or "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By alkyl and lower alkyl is meant straight and branched chain alkyl groups having from 1–6 carbon atoms.

By lower alkoxy and alkoxy is meant straight and branched chain alkoxy groups having from 1–6 carbon atoms.

By heteroaryl is meant 5, 6, or 7 membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be unsubstituted or substituted with e.g., halogen, lower alkyl, lower alkoxy, lower alkylthio, trifluoromethyl, lower acyloxy, aryl, heteroaryl, and hydroxy.

By halogen is meant fluorine, chlorine, bromine and iodine.

By arylalkyl and aralkyl is meant the group —R—Ar where Ar is an aryl group and R is a straight or branched chain aliphatic group. Arylalkyl groups may optionally be substituted with, e.g., halogen, lower alkyl, lower alkoxy, lower alkylthio, trifluoromethyl, lower acyloxy, and hydroxy. Preferred arylalkyl groups in the above formulas where W is CH and $R_8$ represents arylalkyl are phenylalkyl groups where the alkyl portion is lower alkyl. A particularly preferred phenylalkyl group is benzyl where the phenyl ring may be substituted with up to three substituents independently selected from hydrogen, halogen, trifluoromethyl, hydroxy, straight or branched chain lower alkyl having 1–6 carbon atoms, or straight or branched chain lower alkoxy having 1–6 carbon atoms.

By cycloalkyl is meant cyclic hydrocarbons having from 3–8 carbon atoms. These cyclic hydrocarbon groups may be substituted with up to three substituents independently selected from hydrogen, halogen, trifluoromethyl, cyano, straight or branched chain lower alkyl having 1–6 carbon atoms, hydroxy, straight or branched chain lower alkyl having 1–6 carbon atoms, straight or branched chain lower alkoxy having 1–6 carbon atoms, or $SO_2R_9$ where $R_9$ is $NH_2$ or $NHCH_3$.

The pharmaceutical utility of compounds of this invention are indicated by the following assays for dopamine receptor subtype affinity.

Assay for D2 and D3 Receptor Binding Activity

Striatial tissue is dissected from adult male Sprague Dawley rats or BHK 293 cells are harvested containing recombinantly produced D2 or D3 receptors. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.5 ml of tissue sample, 0.5 nM $^3$H-raclopride and the compound of interest in a total incubation of 1.0 ml. Nonspecific binding is defined as that binding found in the presence of $10^{-4}$ M dopamine; without further additions, nonspecific binding is less than 20% of total binding. The binding characteristics of examples of this patent are shown in Table 1 for rat striatal homogenates.

TABLE I

| Compound Number[1] | D2 binding IC$_{50}$($\mu$M) | D3 binding IC$_{50}$($\mu$M) |
| --- | --- | --- |
| 1 | 0.175 | 0.329 |
| 3 | 0.012 | 0.012 |
| 4 | 0.005 | 0.061 |
| 5 | ND | 2.490 |
| 6 | ND | 6.120 |
| 7 | ND | 0.342 |
| 8 | 1.940 | ND |
| 9 | 0.290 | ND |
| 10 | ND | 1.140 |
| 11 | ND | 1.612 |

[1]Compound numbers relate to compounds shown in FIG. I.
ND = Not Done

Assay for D4 Receptor Binding Activity

Clonal cell lines expressing the human dopamine D4 receptor subtype were harvested in PBS and the cells centrifuged and the pellets stored at −80° C. until used in the binding assay. The pellets were resuspended and the cells lysed at 4° C. in 50 mM Tris pH 7.4 buffer containing 120 mM NaCl, 1 mM EDTA and 5 mM $MgCl_2$. The homogenate is centrifuged at 48000×g for 10 minutes at 4° C. The resulting pellet is resuspended in fresh buffer and centrifuged again. After resuspension of the pellet in fresh buffer a 100 ml aliquot is removed for protein determination. The remaining homogenate is centrifuged as above, the supernatant removed and the pellet stored at 4° C. until needed; at which time it is resuspended to a final concentration of 625 mg/ml (250 mg per sample) with 50 mM Tris buffer (pH 7.4) and 120 mM NaCl just prior to use. Incubations were carried out for 60 minutes at 25° C. in the presence of 0.1 nM [$^3$H] YM-09151-2. The incubation was terminated by rapid filtration through Whatman GF/C filters and rinsed with 2×4 ml washes of chilled 50 mM Tris (pH 7.4) and 120 mM NaCl. Non-specific binding was determined with 1 mM spiperone and radioactivity determined by counting in an LKB beta counter. Binding parameter were determined by non-linear least squares regression analysis, from which the inhibition constant Ki could be calculated for each test compound. The binding characteristics of some examples of this patent are shown in Table 2 for the dopamine D4 binding assay. In general, compounds of the accompanying examples were tested in the above assay, and all were found to possess a Ki value for the displacement of [$^3$H]YM-09151-2 from the human dopamine D4 receptor subtype of below 500 nM. Some specific data is indicated in Table 2.

TABLE 2

| Compound Number[1] | Ki($\mu$M) |
| --- | --- |
| 1 | 0.032 |
| 2 | 0.243 |
| 3 | 0.018 |
| 4 | 0.028 |
| 5 | 0.286 |
| 6 | >0.075 |
| 7 | >0.075 |
| 8 | 1.055 |
| 9 | 0.056 |
| 10 | 0.769 |
| 11 | 0.600 |

Compounds, 1, 3, 4 and 9 particularly preferred embodiments of the present invention because of their potency in binding to dopamine receptor subtypes.

The compounds of the invention including those represented by general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol. propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of representative aminomethyl biphenyls, aminomethyl phenyl pyridines and aminomethyl phenyl pyrimidines of the present invention is given in Scheme I. Those having skill in the art will recognize that the starting materials may be varied and additional steps employed to produce compounds encompassed by the present invention. The substituents R', $R_1$, $R_2$, $R_3$, S, T, V, X, Y, and Z carry the definitions set forth above for Formula I.

SCHEME 1

A. Representative preparations of Aminomethyl Biphenyls

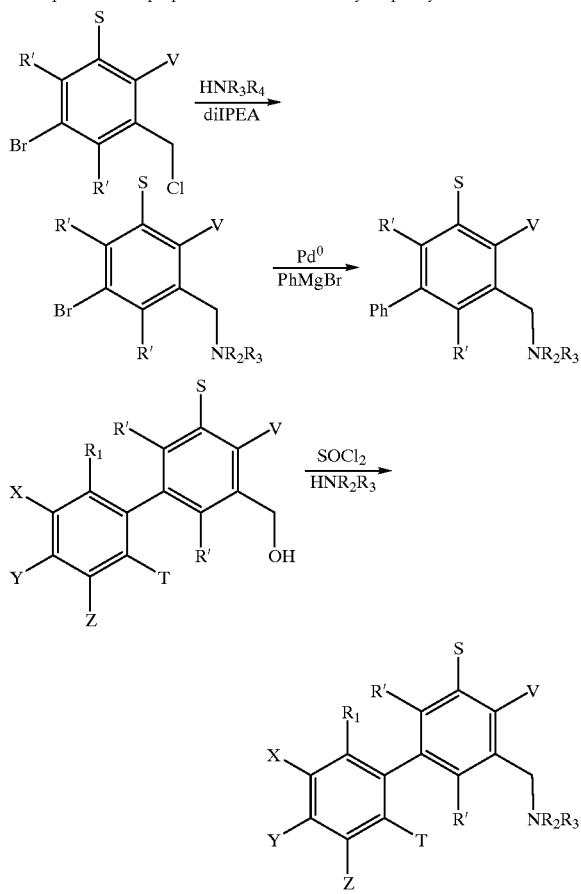

B. Representative preparation of Aminomethyl Phenyl Pyridines

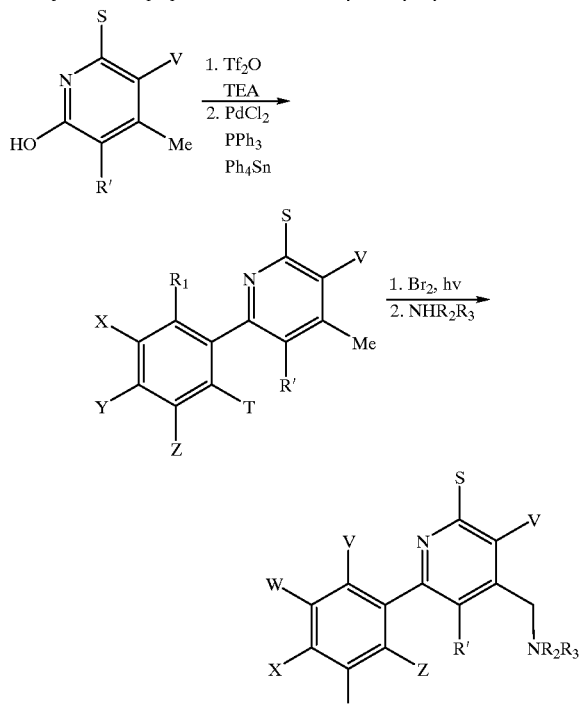

C. Representative preparation of Aminomethyl Phenyl Pyrimidines

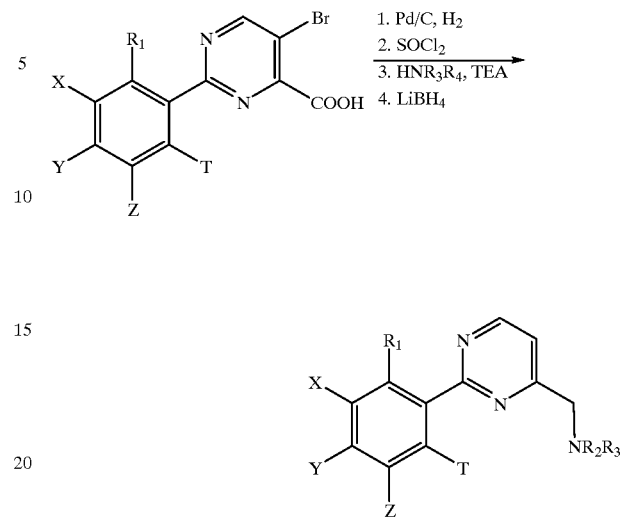

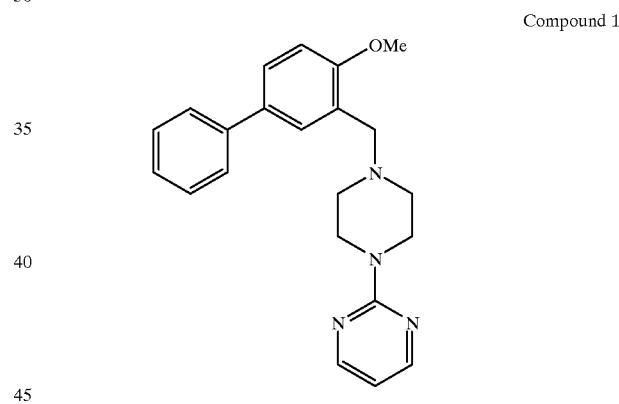

This invention is further illustrated by the following examples which are not to be construed as limiting the invention in scope or spirit to the specific procedures and compounds described therein.

EXAMPLE I

Compound 1

A mixture of 1.1 g of 2-(chloromethyl)-4-bromoanisole, 1 g of 1-(2-pyrimidyl)piperazine dihydrochloride and 2.0 mL N,N-diisopropylethylamine in 10 mL chloroform was heated at reflux temperature for 2 hr, cooled to room temperature, washed with 1N NaOH and water. The solvent was removed by evaporation under reduced pressure to yield 3.6 g of 2-[(4-(2-pyrimidinyl)-piperazinyl)methyl]-4-bromoanisole as a white solid which was used in the next step without further purification.

A solution of 182 mg 2-[(4-(2-pyrimidinyl)-piperazinyl) methyl]-4-bromoanisole in 1 mL of tetrahydrofuran heated to 60° C. and 6 mg of Pd(PPh$_3$)$_4$ was added. To this mixture 0.5 mL of a 1 M solution of phenylmagnesium bromide in tetrahydrofuran was added dropwise. The reaction mixture was heated at relux temperature under nitrogen for 1 hr, cooled to room temperature and the solvent removed by evaporation under reduced pressure to yield 4-phenyl-2-[(4-(2-pyrimidinyl)-piperazinyl)methyl]anisole which was purified by chromatography on silica gel using 5% methanol in dichloromethane as eluent. Evaporation of the solvent yielded 140 mg of a solid which was treated with ethyl acetate-HCl to give 50 mg of 4-phenyl-2-[(4-(2-pyrimidinyl)-piperazinyl)methyl]anisole dihydrochloride (Compound 1), mp 205–207° C.

EXAMPLE II

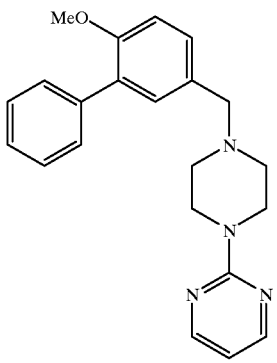

Compound 2

A mixture of 1.1 g of 4-(chloromethyl)-2-bromoanisole 1.0 g 1-(2-pyrimidyl)piperazine dihydrochloride and 2.0 mL of N,N-diisopropylethylamine in 10 mL chloroform was heated at reflux temperature for 2 hr, cooled to room temperature, washed with 1N NaOH and water. The solvent was removed by evaporation under reduced pressure to give 3.4 g of 4-[(4-(2-pyrimidinyl)-piperazinyl)methyl]-2-bromoanisole as a white solid which was used in the next step without further purification or characterization.

To a solution of 181 mg 4-[(4-(2-pyrimidinyl)-piperazinyl)methyl]-2-bromoanisole in 2 mL of dimethylformamide was added phenylboric acid (91.5 mg), triethylamine (152 mg), palladium acetate (3.4 mg) and triphenylphosphine (8.1 mg). The reaction mixture was heated at 100° C. under nitrogen for 4 hr, cooled to room temperature and partitioned between dilute ammonium hydroxide and dichloromethane. The organic layer was washed with water and the solvent removed by evaporation under reduced pressure to 2-phenyl-4-[(4(2-pyrimidinyl)-piperazinyl)methyl] anisole which was purified by reverse phase chromatography on C18 resin using a methanol-water mixture (4:1) as eluent.

Evaporation of the solvent yielded 10 mg of a solid which was treated with ethereal-HCl to give 10 mg of 2-phenyl-4-[(4-(2-pyrimidinyl)-piperazinyl)methyl] anisole dihydrochloride (Compound 2), mp 213–215° C.

EXAMPLE III

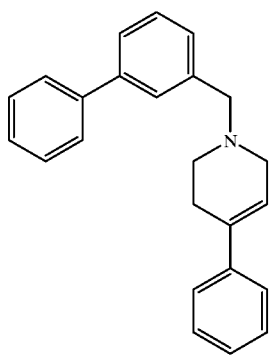

Compound 3

To a suspension of 100 mg of lithium aluminum hydride in 20 mL of ether was added 500 mg 3-phenylbenzoic acid. The reaction mixture was stirred at room temperature overnight. After any excess lithium aluminum hydride was destroyed with water, the organic layer was washed successively with 25 mL aliquots of dilute hydrochloric acid, dilute sodium hydroxide and brine. The organic phase was dried over anhydrous sodium sulfate and the solvent removed by evaporation under reduced pressure to yield 360 mg of 3-hydroxymethylbiphenyl as a crystalline solid. This material was used in the next step without further purification.

A solution of 50 mg of 3-hydroxymethylbiphenyl in 1.5 mL thionyl chloride was heated at reflux temperature for 4 hr, cooled to room temperature and the solvent removed by evaporation under reduced pressure to yield 45 mg of 3-chloromethylbiphenyl which was used in the next step without further purification or characterization.

To a solution of 45 mg of 3-chloromethylbiphenyl in 5 mL of chloroform was added 50 mg of 4-phenyl-1,2,3,6-tetrahydropyridine hydrochloride and 0.5 mL triethylamine. The reaction mixture was heated at reflux temperature overnight, cooled to room temperature, washed successively with 50 mL aliquots of dilute sodim hydroxide and brine. The chloroform was removed by evaporation under reduced pressure to yield 3-phenyl[(4-phenyl-1,2,3,6-tetrahydropyridin-1-yl)methyl]benzene which was purified by chromatography on silica gel using 5% methanol in dichloromethane as eluent. Evaporation of the solvent yielded a solid which was treated with ethereal-HCl to give 15 mg of 3-[(4-1,2,3,6-tetrahydropyridin-1-yl)methyl] biphenyl hydrochloride (Compound 3), mp 236–238° C.

EXAMPLE IV

The following compounds were prepared essentially according to the procedure described in Example III.
(a) 3-[(4-phenyl-piperidin-1-yl)methyl]biphenyl hydrochloride (Compound 4).
(b) 3-phenyl-6-[(4-benzyl-piperidin-1-yl)methyl] toluenehydrochloride (Compound 5), mp 215–217° C.
(c) 3-[(N-methyl-N-benzyl)aminomethyl]biphenyl hydrochloride, mp 184–187° C.
(d) N-(1-(3-biphenyl)ethyl-N-methylbenzylamine hydrochloride (Compound 6), mp 143–145° C.
(e) 1-(2-methoxyphenyl)-4-(1-(3-biphenyl)ethyl)piperazine dihydrochloride (Compound 7), mp 181–183° C.
(f) 1-(2-pyrimidyl)-4-((3,5-diphenylphenyl)methyl) piperazine dihydrochloride (Compound 8), mp 212–214° C.

EXAMPLE V

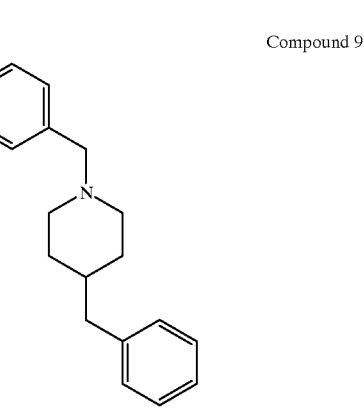

Compound 9

To a solution of 5.0 g of 2-hydroxy-4-methylpyridine in 70 mL of pyridine at 0° C. was added 13.3 g triflic anhydride dropwise. The reaction was stirred at 0° C. for 15 minutes and then allowed to warm to room temperature. After removal of the volatile reactants under reduced pressure, the residue was partitioned between 100 mL of ethyl acetate and 100 mL of 10% sodium carbonate solution. The organic layer was washed with 100 mL of brine and the solvent removed by evaporation under reduced pressure. The resulting oil was vacuum distilled at 150° C. (25 mm Hg) to provide 10.5 g of 2-trifluoromethanesulfonyl-4-methylpyridine as a colorless oil.

To a solution of 1.65 g 2-trifluoromethanesulfonyl-4-methylpyridine in 30 mL of dimethylformamide and 30 mL of dioxane was added PdCl$_2$(PPh$_3$)$_2$ (400 mg), lithium chloride (873 mg) and tetraphenyltin (10.5 g). The reaction mixture was heated at reflux temperature for 3 hr, cooled to room temperature and filtered. The filtrate was diluted with 1N hydrochloric acid, washed with 250 mL ether, then basified with 2N sodium hydroxide and extracted with 2×250 mL of ethyl acetate. The combined extracts were washed with 150 mL water, separated and the ethyl acetate removed by evaporation under reduced pressure to yield 900 mg of 2-phenyl-4-methylpyridine as an oil.

To a solution of 100 mg of 2-phenyl-4-methylpyridine in 2 mL of carbon tetrachloride was added 300 mg of sodium carbonate and 100 mg of bromine. The reaction mixture was stirred and irradiated with a 500 W lamp for 1 h, filtered and the solvent removed by evaporation under reduced pressure to yield 2-phenyl-4-bromomethylpyridine which was used in the next step without further purification or characterization To a solution of 2-phenyl-4-bromomethylpyn'dine in 5 mL of chloroform was added 100 mg of 4-benzylpiperidine and 1 mL of N,N-diisopropylethylamine. The reaction mixture was heated at reflux temperature for 30 minutes, cooled to room temperature, washed with 5 mL of 1N NaOH and the solvent removed by evaporation under reduced pressure. The product was purified by chromatography on silica gel using 5% methanol in dichloromethane as eluent. Evaporation of the solvent yielded a solid which was treated with ethereal-HCl to give 15 mg of 2-phenyl-4-[(4-benzyl-piperidin-1-yl)methyl]-pyridine dihydrochloride (Compound 9), mp 222–225° C.

EXAMPLE VI

The following compound was prepared essentially according to the procedure described in Example V.

(a) 2-Phenyl-6-[(4-benzyl-piperidin-1-yl)methyl]-pyridine (Compound 10), mp 81–83° C.

EXAMPLE VII

Compound 11

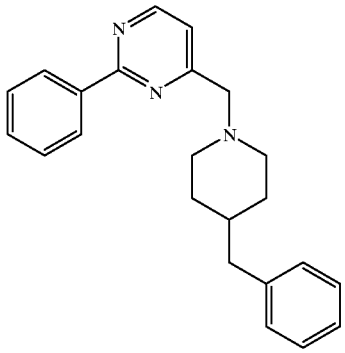

A solution of 500 mg 5-bromo-2-phenyl-4-pyrimidinecarboxylic acid and 1 mL N,N-diisopropylethylamine in 5 mL of ethanol was hydrogenated at 40 psi of H$_2$ for 16 hr using 200 mg of 10% palladium-on-carbon as catalyst. The catalyst was filtered off and the ethanol removed by evaporation under reduced pressure. The residue was dissolved in water, acidified with 3N hydrochloric acid and the precipitate was collected by filtration. This material was air dried to yield 300 mg of 2-phenyl-4-pyrimidinecarboxylic acid as a white solid which was used in the next step without further purification or characterization. A solution of 150 mg of 2-phenyl-4-pyrimidinecarboxylic acid in 1 mL of thionyl chloride was heated at 70° C. for 1 hr, cooled to room temperature and the excess thionyl chloride removed by evaporation under reduced pressure to yield 145 mg of 2-phenyl-4-pyrimidinecarboxylic acid chloride which was used in the next step without further purification or characterization.

To a solution of 145 mg of 2-phenyl-4-pyrimidinecarboxylic acid chloride in 5 mL tetrahydrofuran was added excess lithium borohydride. The reaction mixture was stirred at room temperature for 10 minutes then diluted with 25 mL of ethyl acetate and filtered. The filtrate was washed successively with 25 mL aliquots of 1N sodium hydroxide and brine. The solvent was removed by evaporation under reduced pressure to yield 100 mg of 2-phenyl-4-hydroxymethylpyrimidine as a white solid.

A solution of 55 mg 2-phenyl-4-hydroxymethylpyrimidine in 1 mL of thionyl chloride was heated at reflux temperature for 1 hr and the excess thionyl chloride removed by evaporation under reduced pressure to yield 50 mg of 2-phenyl-4-chloromethylpyrimidine as an oil which was used in the next step without further purification or characterization.

To a solution of 50 mg of 2-phenyl-4-chloromethylpyrimidine in 5 mL chloroform was added 80 mg 4-benzylpiperidine and 1 mL of N,N-diisopropylethylamine. The reaction mixture was heated at reflux temperature for 4 hr, cooled to room temperature, washed with 5 mL 1N sodium hydroxide solution and the solvent removed by evaporation under reduced pressure to yield 2-phenyl-4-[(4-benzyl-piperidin-1-yl)methyl]-pyrimidine. This material was purified by chromatography on silica gel using 5% methanol in dichloromethane as eluent. Evaporation of the solvent yielded a solid which was treated with ethereal-HCl to give 15 mg of 2-phenyl-4-[(4-benzyl-piperidin-1-yl)methyl]-pyrimidine dihydrochloride (Compound 11), mp 211–213° C.

EXAMPLE VIII

The following compound was prepared essentially according to the procedure described in Example VII.

(a) 2-phenyl-4-[(N-methyl-N-benzyl)aminomethyl]-pyrimidine dihydrochloride (Compound 12).

The disclosures in this application of all articles and references, including patents, are incorporated herein by reference.

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude the specification.

What is claimed is:

1. A compound of the formula:

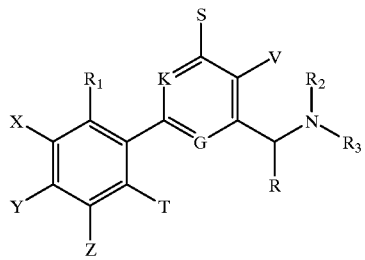

or a pharmaceutically acceptable salt thereof wherein:
S and V are the same or different and represent hydrogen, halogen, hydroxy, phenyl, straight or branched chain lower alkyl having 1–6 carbon atoms, or straight or branched chain lower alkoxy having 1–6 carbon atoms;
G and K represent N or CR' where R' is hydrogen, halogen, straight or branched chain lower alkyl having 1–6 carbon atoms or straight or branched lower alkoxy having 1–6 carbon atoms, provided that one and only one of G and K is nitrogen;
R is hydrogen or straight or branched chain lower alkyl having 1–6 carbon atoms;
$R_1$, X, Y, Z and T are the same or different and represent hydrogen, halogen, cyano, hydroxy, straight or branched chain lower alkyl having 1–6 carbon atoms, straight or branched chain lower alkoxy having 1–6 carbon atoms or $SO_2R_4$ where $R_4$ is straight or branched chain lower alkyl having 1–6 carbon atoms or where $R_4$ is $NH_2$ or $NHCH_3$;
$NR_2R_3$ represents

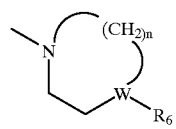

where W is N; and
$R_6$ is phenyl, benzyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; and
n is 1, 2 or 3.

2. A compound of the formula:

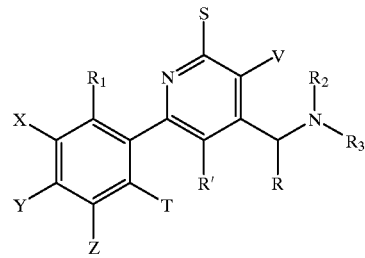

or the pharmaceutically acceptable salts thereof wherein:
S and V are the same or different and represent hydrogen, halogen, hydroxy, phenyl, straight or branched chain lower alkyl having 1–6 carbon atoms, or straight or branched chain lower alkoxy having 1–6 carbon atoms;
R' is hydrogen, halogen, straight or branched chain lower alkyl having 1–6 carbon atoms or straight or branched lower alkoxy having 1–6 carbon atoms;
R is hydrogen or straight or branched chain lower alkyl having 1–6 carbon atoms;
$R_1$, X, Y, Z and T are the same or different and represent hydrogen, halogen, cyano, hydroxy, straight or branched chain lower alkyl having 1–6 carbon atoms, straight or branched chain lower alkoxy having 1–6 carbon atoms or $SO_2R_4$ where $R_4$ is straight or branched chain lower alkyl having 1–6 carbon atoms or where $R_4$ is $NH_2$ or $NHCH_3$;
$NR_2R_3$ represents

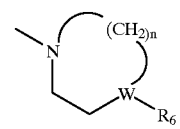

where W is N; and
$R_6$ is phenyl, benzyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; and n is 1, 2 or 3.

3. A compound of the formula:

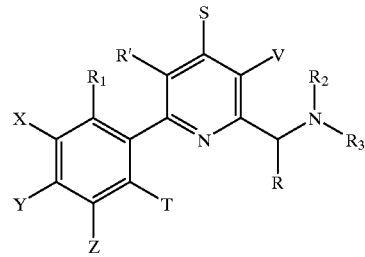

or the pharmaceutically acceptable salts thereof wherein:
S and V are the same or different and represent hydrogen, halogen, hydroxy, phenyl, straight or branched chain lower alkyl having 1–6 carbon atoms, or straight or branched chain lower alkoxy having 1–6 carbon atoms;

R' is hydrogen, halogen, straight or branched chain lower alkyl having 1–6 carbon atoms or straight or branched lower alkoxy having 1–6 carbon atoms;

R is hydrogen or straight or branched chain lower alkyl having 1–6 carbon atoms;

$R_1$, X, Y, Z and T are the same or different and represent hydrogen, halogen, cyano, hydroxy, straight or branched chain lower alkyl having 1–6 carbon atoms, straight or branched chain lower alkoxy having 1–6 carbon atoms or $SO_2R_4$ where $R_4$ is straight or branched chain lower alkyl having 1–6 carbon atoms or where $R_4$ is $NH_2$ or $NHCH_3$;

$NR_2R_3$ represents

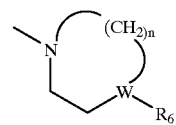

where W is N; and $R_6$ is phenyl, benzyl, pyridyl or pyrimidinyl, unsubstituted or mono or disubstituted with halogen, hydroxy, straight or branched chain lower alkyl having 1–6 carbon atoms, or straight or branched chain lower alkoxy having 1–6 carbon atoms; and n is 1, 2 or 3.

* * * * *